(12) United States Patent
Burpee et al.

(10) Patent No.: US 6,520,985 B1
(45) Date of Patent: *Feb. 18, 2003

(54) STENT WITH REDUCED SHORTENING

(75) Inventors: Janet Burpee, Fair Haven, NJ (US); David R. Fischell, Fair Haven, NJ (US)

(73) Assignee: Cordis Corporation, Warren, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 09/688,157

(22) Filed: Oct. 16, 2000

Related U.S. Application Data

(63) Continuation of application No. 09/049,556, filed on Mar. 27, 1998.

(51) Int. Cl.[7] .................................................. A61F 2/06
(52) U.S. Cl. ....................................................... 623/1.11
(58) Field of Search ................................. 623/1.1, 1.11, 623/1.12, 1.13, 1.14, 1.15, 1.16, 1.17, 1.18, 1.19, 1.2, 1.21, 1.22; 606/108, 191, 194, 198

(56) References Cited

U.S. PATENT DOCUMENTS

| | | | | |
|---|---|---|---|---|
| 5,807,404 A | * | 9/1998 | Richter | ............................ 623/1 |
| 5,827,321 A | * | 10/1998 | Roubin et al. | ............... 606/198 |
| 5,855,600 A | * | 1/1999 | Alt | .................................. 623/1 |
| 6,059,811 A | * | 5/2000 | Pinchasik et al. | ........... 606/198 |
| 6,203,569 B1 | * | 3/2001 | Wijay | ......................... 623/1.15 |

* cited by examiner

Primary Examiner—Michael J. Milano
Assistant Examiner—Vy Q. Bui
(74) Attorney, Agent, or Firm—Rosenberg, Klein & Lee

(57) ABSTRACT

A balloon expandable metal stent is provided that includes a multiplicity of circumferential sets of strut members wherein at least two adjacent circumferential sets of strut members are coupled together by a plurality of undulating longitudinal struts. The stent is annealed to a degree where frictional forces existing in the longitudinal direction between adjacent circumferential sets of strut members and the balloon, during inflation, are greater than a force required to permanently deform the undulating longitudinal struts. Thus, the expansion of the space between adjacent circumferential sets of strut members during inflation of the balloon compensates for shortening of the stent that would otherwise occur during radial expansion of the stent responsive to the inflation of the balloon. The undulating longitudinal struts also have a width dimension throughout their length which is less than a width dimension of the circumferential sets of strut members to further facilitate the deformation of the undulating longitudinal struts when the balloon is inflated.

6 Claims, 2 Drawing Sheets

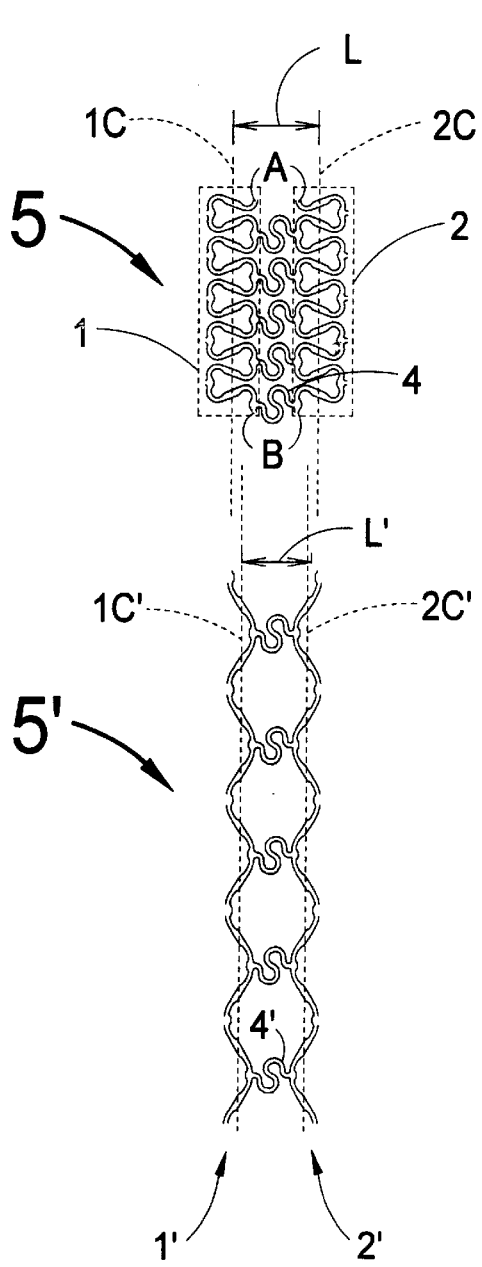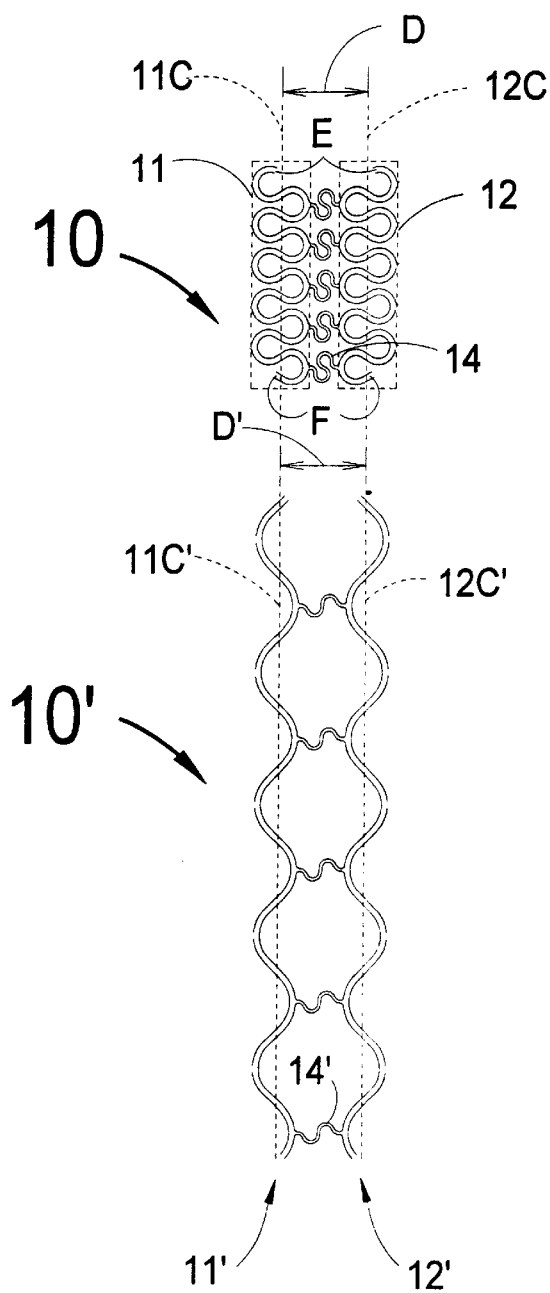
"PRIOR ART"
FIG. 1
FIG. 2

STENT WITH REDUCED SHORTENING

This application is a continuation of copending application(s) application Ser. No. 09/049,556 filed on Mar. 27, 1998.

FIELD OF USE

This invention is in the field of stents that are used to maintain patency of a vessel of the human body.

BACKGROUND OF THE INVENTION

It has been shown that intravascular stents are an excellent means to maintain the patency of blood vessels following balloon angioplasty. Robert, David and Tim Fischells in U.S. Pat. No. 5,695,516 describe a stent design which elongates as it begins expansion. The Fischells in U.S. Pat. No. 5,697,971 describe a stent which also elongates as it begins to expand and includes "S" shaped undulating longitudinal structures to enhance flexibility and side branch access. Both these designs lengthen at first then shorten as they expand to larger diameters. Beyond a certain point, these designs can actually shorten more than designs which do not initially lengthen.

SUMMARY OF THE INVENTION

This invention is an improvement of the stent design described in U.S. Pat. No. 5,697,971 to reduce shortening during stent expansion. The present invention is a balloon expandable stent made from either fully annealed stainless steel or a metal of equivalent "softness". This stent also has expandable circumferential sets of strut members connected by undulating longitudinal structures such as those of the prior art. The present invention is different in that the undulating longitudinals are specifically adapted to stretch during balloon expansion so as to reduce stent shortening.

Because friction exists between the balloon and the stent's inside surface as the stent is expanded by the balloon, each circumferential set of strut members will tend to maintain its longitudinal position on the balloon. If there were no interconnections between the circumferential sets of strut members, the average distance between the circumferential sets of strut members would stay the same and each set of strut members would decrease in its longitudinal dimension. The relatively stiff undulating longitudinal structures of the prior art which resist stretching will pull the circumferential sets of strut members toward each other as the stent expands causing the stent to shorten. If however, the undulating longitudinal structures are weak and easily stretched by forces less than the friction between each circumferential set of strut members and the balloon, then the undulating longitudinal structures will be permanently elongated. If as the stent expands, the circumferential sets of strut members maintain their longitudinal position, and the undulating longitudinal structures stretch to compensate for the longitudinal shortening of each circumferential set of strut members, then the stent will barely shorten.

Thus it is an object of this invention to have a stent with reduced shortening as a result of the permanent longitudinal stretching of undulating longitudinal structures as the stent is radially expanded.

Another object of this invention is to have the frictional forces between adjacent circumferential sets of strut members and the balloon being sufficiently great during balloon inflation so that the metal of the undulating longitudinal structures that connect adjacent sets of strut members is stressed beyond its elastic limit.

Still another object of this invention is to have the width of the undulating longitudinal structures be significantly less than the width of other stent struts.

These and other objects and advantages of this invention will become obvious to a person of ordinary skill in this art upon reading of the detailed description of this invention including the associated drawings.

BRIEF DESCRIPTION OF THE DRAWINGS

FIG. 1 is a flat layout view of two connected circumferential sets of strut members of a prior art stent both before and after balloon expansion.

FIG. 2 is a flat layout view of two connected circumferential sets of strut members of the present invention stent both before and after balloon expansion.

DETAILED DESCRIPTION OF THE DRAWINGS

Figure 3:
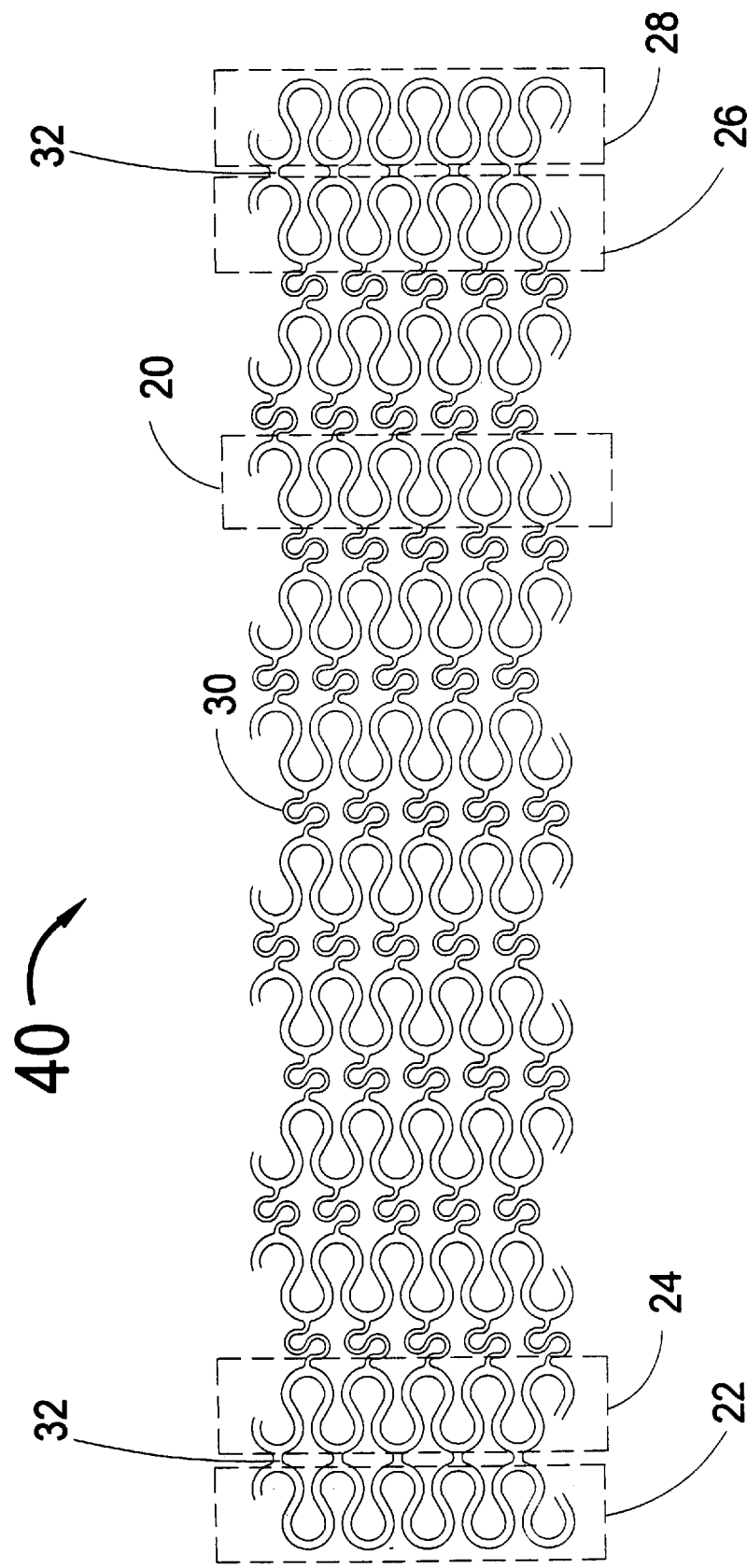
FIG. 3 is a flat layout view of a complete stent of the present invention before balloon expansion with connected circumferential sets of strut members similar to those shown in FIG. 2.

FIG. 1 is a flat layout view of an unexpanded cylindrical section 5 and radially expanded cylindrical section 5' of the prior art stent described in U.S. Pat. No. 5,697,971. The unexpanded section 5 has two circumferential sets of strut members 1 and 2. When the two sets of strut members 1 and 2 are actually in their cylindrical shape, the points "A" are connected to points "B". Five "S" shaped undulating longitudinals 4 connect the two circumferential sets of strut members 1 and 2 to each other. In the section 5, the widths of the circumferential sets of strut members 1 and 2 are similar to that of the "S" shaped undulating longitudinals 4. The centerline of the circumferential sets of strut members 1 and 2 are shown as the dashed lines 1C and 2C respectively. The separation length between the two center lines 1C and 2C is shown as "L" at the top of FIG. 1.

When the prior art stent expands, the cylindrical section 5 becomes the cylindrical section 5' with the circumferential sets of strut members 1' and 2' having centerlines 1C' and 2C' respectively with separation "D'" and "S" shaped undulating longitudinals 4'. If the circumferential sets of strut members 1' and 2' were not connected via the "S" undulations 4', the centerlines 1C' and 2C' would not move with respect to each other as the stent expands during balloon inflation. This is not true however, when the circumferential sets of strut members 1' and 2' are interconnected. Because of their relatively thick widths, the "S" undulations 4' tend to keep the same shape as the pre-expansion "S" undulation 4. As a result, the circumferential sets of strut members 1' and 2' are pulled toward each other during stent expansion by the "S" undulations 4. This causes the separation "L'" to be less than the separation "L" of the centerlines 1C and 2C of the unexpanded stent section 5. When one considers that an entire stent might have 10 or more circumferential sets of strut members per centimeter of length, the overall shortening can become appreciable.

FIG. 2 is a flat layout view of an unexpanded cylindrical section 10 and expanded cylindrical section 10' of the present invention stent. The unexpanded section 10 has two circumferential sets of strut members 11 and 12. The points "E" are connected to points "F" when the section 10 is in its cylindrical form. Five narrow "S" shaped undulating longitudinals 14 connect the circumferential sets of strut members 11 and 12 to each other. In this stent section 10, the widths of the circumferential sets of strut members 11 and 12 are approximately twice that of the "S" shaped undulating longitudinals 14. What is most important is that the "S" longitudinals are easily extended in the longitudinal direction when a force is applied at their ends. The centerline of the circumferential sets of strut members 11 and 12 are shown as the dashed lines 11C and 12C respectively with separation distance "D".

When the present invention stent expands, the cylindrical section 10 becomes the cylindrical section 10' with circumferential sets of strut members 11' and 12' having centerlines 11C' and 12C' respectively with separation distance "D'" and elongated "S" shaped undulating longitudinals 14'. If the circumferential sets of strut members 11' and 12' were not connected via the "S" undulations 14', the centerlines 11C' and 12C' would not move with respect to each other as the stent is balloon expanded. If during stent expansion the frictional force between the balloon used for expansion (not shown) and each of the two adjacent circumferential sets of strut members 11' and 12' is greater than the force required to stretch the thin "S" undulations 14', the centerlines 11C' and 12C' will not move toward each other as in the prior art stent of FIG. 1. Instead, the "S" undulations 14' will stretch (as shown in FIG. 2) so that the centerline separation "D'" of the post-expansion stent section 10' will be the same as the centerline spacing "D" of the pre-expansion stent section 10; i.e., the distances "D'" and "D" will be essentially the same. Thus, a stent consisting of a multiplicity of such cylindrical sections 10 would not appreciably change its length when it is radially expanded by an inflated balloon.

The reason that the undulating longitudinal struts 14' are permanently extended in the longitudinal direction is that the frictional force in the longitudinal direction between the pair of sets of stent members 11' and 12' and the balloon during balloon inflation is greater than the force required to stress the metal of the struts 14' beyond its elastic limit. Ideally, extended struts 14' should be at least 50 percent longer in the longitudinal direction compared to the struts 14 after balloon inflation to a balloon diameter of at least 3.0 mm. However, a longitudinal length increase of as little as 10 percent for each undulating longitudinal strut 14' would provide a significant reduction in the longitudinal shortening of an entire stent when the balloon is expanded to at least a 3.0 mm diameter.

FIG. 3 is a flat layout view of the entire stent 40 of the present invention. The stent 40 has twelve, cylindrically shaped circumferential sets of strut members 20 connected by either "S" undulating longitudinals 30 or by straight links 32. Straight links 32 are used to connect the circumferential sets of strut members 22 and 24 at the proximal end of the stent 40 and circumferential sets of strut members 26 and 28 at the distal end of the stent 40. Straight links 32 enhance the strength of the end circumferential sets of strut members 22 and 28. The thin "S" undulating longitudinals 30 enhance the flexibility of the stent 40. The comparatively narrow width of the "S" undulating longitudinals 30 allow these comparatively weak "S" undulations to stretch in length as the stent 40 is radially expanded. This stretching compensates for the shortening in the longitudinal direction of the circumferential sets of strut members 20 as they unfold during stent expansion. Typical strut width for the circumferential sets strut members 20 is 0.15 mm (0.006 in). Typical strut width for the thin "S" undulating longitudinals 30 is 0.075 mm (0.003 in). The stent in FIG. 3 is designed to be a 25 mm long coronary stent having an unexpanded diameter of approximately 1.5 mm and an expanded diameter range of 2 to 6 mm. Similar designs cut from larger tubing or with some modifications can be used for stenting of the biliary duct, a peripheral vessel or other applications. Although the stent 40 shows 5 cells circumferentially, a similar could be produced with anywhere from 3 to 9 circumferential cells for each circumferential set of strut members 20.

The stent 40 is typically laser cut from 316L stainless steel tubing having a wall thickness between 0.05 mm and 0.2 mm. To facilitate the "S" stretching, a stent made from 316L stainless steel should be fully annealed so that the elastic limit of the metal is readily exceeded when even a comparatively small force is exerted on the undulating longitudinal struts.

Although the design described in FIGS. 2 and 3 utilizes the narrow width "S" undulations 14 and 30 to facilitate "S" stretching, it is also envisioned that using undulations of reduced wall thickness or of softer metal could produce the same effect. It is also envisioned that the undulating longitudinals need not have an "S" shape. "U", "V", "W" or any combination of S, U, V and/or W or equivalent shapes would produce the same desirable effects of enhanced flexibility and permanent stretching during stent expansion. Stents of this design will shorten the least when the force required to elongate the undulating longitudinals is significantly less than the frictional forces between the balloon used for the required expansion and each of the circumferential sets of strut members. Therefore, it is desirable to avoid balloon coatings that are lubricous which would decrease such frictional forces.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A combination balloon expandable stent and inflatable balloon onto which the stent is coaxially mounted, the stent consisting of a multiplicity of cylindrical sections with each cylindrical section consisting of two, adjacent circumferential sets of strut members joined by a multiplicity of undulating longitudinal structures, each of said undulating longitudinal structures being coupled on opposing ends thereof to a pair of consecutively located sets of strut members, each of said undulating longitudinal structures being approximately one-half the width of the strut member forming a respective set of strut members, the stent having an expanded diameter between 2 and 6 mm, the undulating longitudinal structures being characterized by being sufficiently weak so that when the balloon is inflated, the frictional force in the longitudinal direction between each of the two circumferential sets of strut members and the balloon is sufficient to cause a permanent increase in the longitudinal length of each undulating longitudinal structure by at least 10 percent thereby reducing the extent of stent shortening when the balloon is inflated.

2. The combination stent and balloon of claim 1 wherein the metal of the stent is fully annealed, the fully annealed state allowing each undulating longitudinal structure to be permanently increased in longitudinal length at a reduced magnitude of frictional force with respect to a frictional force that would be required to extend the undulating structures when the stent is less than fully annealed.

3. The combination stent and balloon of claim 1 wherein the shape of at least a majority of the undulating longitudinal structures is selected from the group that includes one of the following shapes: "S", "U", "V", "W", or any equivalent shape that would produce the same desirable effects of enhanced flexibility and permanent stretching during stent expansion.

4. A combination balloon expandable metal stent and inflatable balloon onto which the stent is coaxially mounted, the stent having a multiplicity of circumferential sets of strut members with one circumferential set of strut members at each end of the stent and at least five central circumferential sets of strut members, each central circumferential set of strut members being joined to an adjacent central circumferential set of strut members by a multiplicity of undulating longitudinal structures, each of said undulating longitudinal structures being coupled on opposing ends thereof to a pair of consecutively located sets of central circumferential strut members, each of said undulating longitudinal structures being approximately one-half the width of the strut member forming a respective central circumferential set of strut members, the stent having an expanded diameter between 2 and 6 mm, the undulating longitudinal structures being characterized by being sufficient weak so that when the balloon is inflated, the frictional force in the longitudinal direction between each adjacent central circumferential set of strut members and the balloon is large enough to permanently increase the longitudinal length of each undulating longitudinal structure by at least 10 percent as a result the frictional force acting on each weak undulating longitudinal structure, the frictional force being sufficiently great so as to cause a stress in each undulating longitudinal structure that exceeds the elastic limit of the metal of the undulating longitudinal structure.

5. The combination stent and balloon of claim 4 wherein the metal of the stent is fully annealed, the fully annealed state allowing each undulating longitudinal structure to be permanently increased in longitudinal length at a reduced magnitude of frictional force with respect to the frictional force that would be required to extend the undulating structure when the stent is less than fully annealed.

6. The combination stent and balloon of claim 4 wherein the shape of at least a majority of the undulating longitudinal structures is selected from the group that includes one of the following shapes: "S", "U", "V", "W", or any equivalent shape that would produce the same desirable effects of enhanced flexibility and permanent stretching during stent expansion.

* * * * *